United States Patent [19]

Mercaldi

[11] Patent Number: 4,845,896
[45] Date of Patent: Jul. 11, 1989

[54] SURFACE SAMPLING DEVICE

[75] Inventor: David W. Mercaldi, Sudbury, Mass.

[73] Assignee: Failure Analysis Associates, Palo Alto, Calif.

[21] Appl. No.: 17,632

[22] Filed: Feb. 24, 1987

[51] Int. Cl.$^4$ .......................... B24B 19/00; G01N 1/04
[52] U.S. Cl. ................................ 51/33 R; 51/206 R;
  51/209 R; 51/99; 51/126; 73/864.41
[58] Field of Search .............. 51/206 R, 209 R, 33 R,
  51/58, 59, 99, 126, 281 R; 81/490, 491;
  73/864.41, 864.81; 83/54, 490, 491, 861, 919;
  125/13.55; 408/150; 409/143

[56] References Cited

U.S. PATENT DOCUMENTS

| | | | |
|---|---|---|---|
| 122,514 | 1/1872 | Bullock | 51/206 R |
| 2,378,870 | 6/1945 | Soetbeer . | |
| 2,600,254 | 6/1952 | Lysobey . | |
| 2,739,368 | 3/1956 | McCall . | |
| 2,743,092 | 4/1956 | Funk . | |
| 2,826,077 | 3/1958 | Walker . | |
| 2,942,092 | 6/1960 | Cammann . | |
| 3,086,410 | 4/1963 | Zimmermann . | |
| 3,094,016 | 6/1963 | Kleine . | |
| 3,108,918 | 10/1963 | Plumley . | |
| 3,109,232 | 11/1963 | Melvin . | |
| 3,159,952 | 12/1964 | Lipkins | 51/209 R |
| 3,169,588 | 2/1965 | Cashen et al. . | |
| 3,184,827 | 5/1965 | Melvin . | |
| 3,186,261 | 6/1965 | Howard et al. . | |
| 3,196,722 | 7/1965 | Lewis et al. . | |
| 3,199,379 | 8/1965 | Korson . | |
| 3,216,153 | 11/1965 | Saville et al. . | |
| 3,223,088 | 12/1965 | Barber et al. . | |
| 3,227,013 | 1/1966 | Zimmermann . | |
| 3,244,035 | 4/1966 | Jehle et al. . | |
| 3,308,689 | 3/1967 | MacDonald . | |
| 3,330,754 | 7/1967 | Trager . | |
| 3,340,166 | 9/1967 | Trager . | |
| 3,365,988 | 1/1968 | Karlan . | |
| 3,374,586 | 3/1968 | Stone | 51/209 R |
| 3,383,296 | 5/1968 | Trager . | |
| 3,548,687 | 12/1970 | Holloway . | |
| 3,603,264 | 9/1971 | Von Arx . | |
| 3,610,768 | 10/1971 | Cochran . | |
| 3,622,734 | 11/1971 | Mainwaring . | |
| 3,622,735 | 11/1971 | Mainwaring . | |
| 3,663,784 | 5/1972 | Mainwaring . | |
| 3,730,634 | 5/1973 | Gerber et al. . | |
| 3,780,435 | 12/1973 | Farha et al. . | |
| 3,811,352 | 5/1974 | McFadden . | |
| 3,857,425 | 12/1974 | Wiklund | 83/490 |
| 3,881,396 | 5/1975 | Case . | |
| 3,909,388 | 9/1975 | Faust et al. . | |
| 3,942,905 | 3/1976 | Gill et al. . | |
| 3,966,349 | 6/1976 | Osman et al. . | |
| 4,106,561 | 8/1978 | Jerome et al. . | |
| 4,107,972 | 8/1978 | Martin . | |
| 4,129,400 | 12/1978 | Wozar . | |
| 4,220,201 | 9/1980 | Hauk . | |
| 4,231,419 | 11/1980 | Gugel . | |
| 4,252,152 | 2/1981 | Martin et al. . | |
| 4,253,497 | 3/1981 | Martin et al. . | |
| 4,271,733 | 6/1981 | Stone . | |
| 4,294,011 | 10/1981 | Kemme . | |
| 4,299,110 | 11/1981 | Martin . | |
| 4,304,139 | 12/1981 | Johnson | 73/864.41 X |
| 4,352,610 | 10/1982 | Yankovoy et al. . | |
| 4,391,118 | 7/1983 | Martin . | |
| 4,434,815 | 3/1984 | Flaherty et al. . | |
| 4,461,947 | 7/1984 | Ward . | |
| 4,500,234 | 2/1985 | Orth et al. . | |
| 4,507,030 | 3/1985 | Jackson . | |
| 4,521,264 | 6/1985 | Mueller . | |
| 4,588,119 | 5/1986 | Fernandez-Acebal et al. . | |
| 4,591,303 | 5/1986 | Sato et al. . | |
| 4,598,597 | 7/1986 | Widner et al. . | |
| 4,602,897 | 7/1986 | Teets . | |
| 4,625,707 | 12/1986 | Whittaker . | |

OTHER PUBLICATIONS

Grimsley's House of Tools Inc, Portsmouth, Virginia, Grimsley's Portable Trepanning Metal Cutting Machine Model WP-1, Jun. 1, 1989.

Primary Examiner—Robert P. Olszewski
Attorney, Agent, or Firm—Hall, Myers & Rose

[57] ABSTRACT

A device, utilizing a unique hemispherical cutter to remove a sample of material and to retain the sample of material for retrieval. The cutter is mounted on a chassis which can travel along the interior or exterior of the device to be sampled. The carriage can be maintained in a fixed position relative to the structure being sampled. After positioning of the cutter carrying carriage the cutter blade is pivoted into engagement with the surface. The blade penetrates the surface and removes a sample in a single continuous cut, leaving a shallow dimple. The sample is then retrieved through the return of the cutter and carriage from the device being sampled.

30 Claims, 5 Drawing Sheets

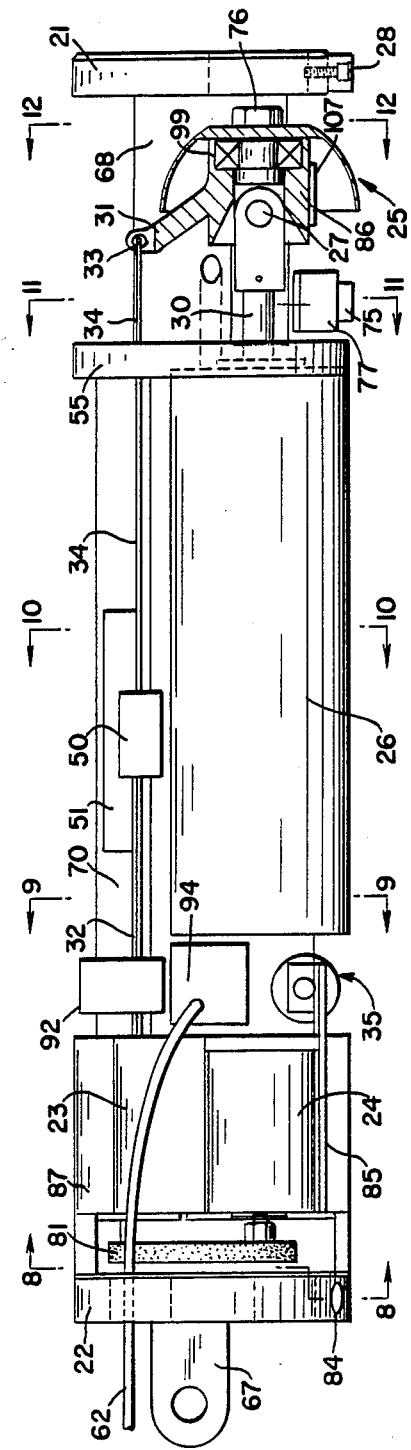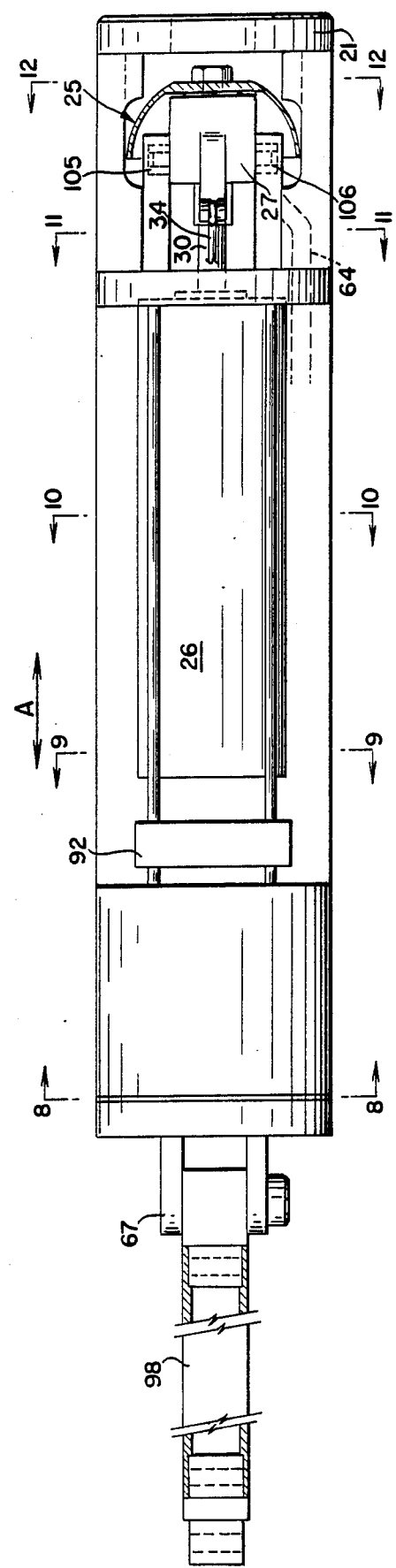

SURFACE SAMPLING DEVICE

BACKGROUND OF THE INVENTION

The present invention relates to devices for obtaining and retrieving a sample of material for analysis. More particularly, the present invention relates to sampling devices which detach and retrieve a portion of the surface of a material for anaylsis of surface features and of the underlying material, such as, for example, of the inner portions of pipes found in electric generating "power" plants.

It is often necessary to test or examine material which has been subjected to a somewhat hostile operating environment. In order to accurately, quantitatively, determine the properties of a material, a sample must be obtained from the material for testing. Further, any detailed metallurgical examination requires a sample of material for laboratory analysis. The need for testing or examination of structural materials in remote locations can arise in a number of situations, including the interior of a pipe or conduit which transports material at temperatures and pressures which can cause changes in the mechanical properties of the material composing the pipe over its service life. Also, other equipment which is subjected to stress, and thermal, radiation, chemical, or other environmental conditions may need to be sampled and tested to determine the damaging effects caused by such conditions.

The effects of exposure to hostile environments, and mechanical and thermal stress can produce severe problems in many situations and with many types of equipment. Notably, an acute problem has developed in aging power plants which have been in service for long periods of time. The turbines which are utilized to generate power from steam are subjected to thermal, mechanical and corrosive stresses. These stresses can cause failure of all or part of a turbine. If no data is available as to the condition of the materials which compose the components of the turbine then an uninformed decision has to be made as to whether to continue to run the turbines without knowing their true condition; thus presenting the undesirable dilemma of either incurring a significant risk of failure or replacing, prematurely, the turbines prior to the expiration of their useful life. Continuing to run a turbine which has unknowingly become unreliable can, of course, result in catastrophic failure. In addition to the potential tragedy of human injury, there is the enormous expense, in such a situation of having to replace the entire turbine, simply because one component failed.

For the above reasons, at least, there is a great need for a means for determining the condition of the material components of turbines and similar mechanical structures which undergo stress over a prolonged period of time. There is in this respect, a great need to be able to predict the remaining useful life of these machines and their material components. Unfortunately, prior to the advent of the present invention, it was often not possible to accurately measure the present condition of materials subjected to long term stress without destroying or significantly deforming the material components of the mechanism to be tested or completely dissembling the mechanism to be inspected. Under certain prior art sampling techniques, for example, great expense and time was necessary to repair the damage done through the sampling process.

Many techniques have been developed in the prior art for obtaining a sample for analysis, in an attempt to mitigate the above problems. None has been truly successful in permitting sample removal from remote locations with minimal structural consequences. One technique, for example, makes two cuts into a surface to form a V-shaped groove in the piece of material to be tested. The cuts are made along the entire length of the material in order for the triangular shaped section of material to be removed from the main portion of the material. If the cuts are not along the entire length, two further cuts are needed at either end in order to release the triangular sample, or, the two cuts may be made by a slightly cupped grinding wheel, yielding a sample shape which is typically described as a "boat sample". These processes require a large sample to be taken from the underlying material, and each leaves a sharp hole which needs later repair. This repair of the underlying material is often time consuming and expensive and will generally result in a weakened structure. Further, performing such an operation remotely is not practical.

Another prior art technique which permits obtaining some information about the material while causing little or no damage to the component is referred to as "replication". In this technique, the surface of the material is replicated by application of a coating, generally after some mechanical polishing and chemical etching of the surface has been performed. The coating is applied in liquid form and allowed to harden and is then peeled off to reveal a mirror image of the surface features of the underlying material. This technique only allows for examination of surface features and does not allow for analysis of the underlying material. Also, it is typically not possible to perform this technique in remote locations. The lack of an actual, physical sample of the underlying material is obviously a significant drawback when attempting to evaluate the condition of certain power plant/turbine components.

As alluded to above, it is also possible to analyze underlying material structures by partial or complete dismantling of the mechanism involved. It may then be possible to examine or sample material components of the mechanism by conventional techniques, followed by replacement of the worn out or damaged parts and reassembly. This often necessitates lengthy shut down periods and requires a large amount of time and expense in the disassembly and reassembly of complicated machinery.

In view of the above, it is apparent that there exists a need in the art for a sampling device which at least overcomes the above-described problems.

SUMMARY OF THE INVENTION

The subject invention, by a unique combination of elements, solves the above-described needs in the art and other needs, apparent to the skilled artisan once given the following disclosure:

It is an object of the present invention to provide a mechanism for obtaining a sample which can be analyzed for surface and/or sub-surface characteristics and to determine the physical parameters of the material from which the sample is taken.

It is a further object of the present invention to provide a device which can separate and retrieve a sample of material with minimal disruption to the underlying structure.

It is still a further object of the present invention to provide a device which can cut a sample from any surface of a solid piece of material.

It is yet another object of the present invention to provide a device which can cut a sample from a solid piece of material and retrieve the sample intact.

It is still another object of the present invention to provide a device which can remove a sample from a solid piece of material without disruption of the original surface of the sample, or of the base material contained in the sample.

These and other objectives are accomplished by the present invention which is comprised of a device for obtaining a sample of a substrate and surface comprising cutting means for separating said sample from said substrate, said cutting means including a generally hemispherically-shaped blade having an axis of rotation generally concentric with the center of said blade, first drive means connected to said blade for rotating said cutter about said axis, second drive means connected to said blade for articulating said cutting means whereby said blade is capable of separating said sample from said substrate by following an arcuate path, and means for retrieving said sample when separated from said substrate.

The present invention creates minimal disruption of the structure from which the sample is taken. A small semi-spherical depression is left in the underlying material in the location from which the sample was removed. The cutter of the present invention allows for a single pass in order to separate the sample from the remainder of the material. The single cut, made from one direction is smooth and continuous and therefore leaves no sharp edges.

The teachings of the present invention illustrate that sharp edges or discontinuities need to be avoided to minimize stress concentration around the sample taken. The depression formed in the underlying material is spherical and shallow thereby presenting the minimal distortion profile attainable.

In certain preferred embodiments, the depth of the cut can be controlled by the relative positioning of the carrier and the structure from which the sample is taken. A very accurate sample can therefore be obtained which maintains the sample surface intact for analysis. The blade in such an embodiment may be designed for minimum abrasive grinding by generation of a thin kerf for passage of the hemispherical blade.

The hemispherical cutter contemplated in certain further embodiments of the present invention may be of a mechanical cutting type, electrical discharge machining type or any other type cutter which can be configured to form a hemispherical cut line creating a minimal thickness kerf for travel of the blade.

A further advantage of the single pass cut of the present invention is that samples can be taken near junctures of differing planes within the mechanism. A cut near such a corner can be made because all drive and support means can be located on one side of the cutter, permitting placement of the cutter itself deep into the corner from one side as opposed to some previously described sampling methods requiring two cuts from opposing directions.

This invention will now be described with respect to certain embodiments as illustrated in the following drawings:

BRIEF DESCRIPTION OF THE DRAWINGS

FIG. 1 is a side view of a preferred embodiment of the present invention.

FIG. 2 is a top view of a preferred embodiment of the present invention.

DETAILED DESCRIPTION OF A PREFERRED EXEMPLARY EMBODIMENT

Figure 4:
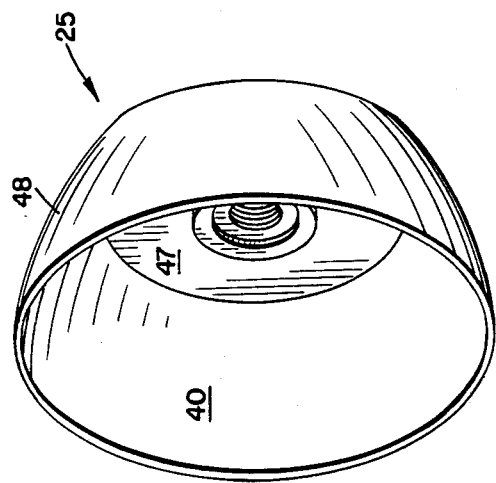
FIG. 4 is a perspective view of a preferred embodiment of the hemispherical cutting blade of the present invention.

FIGS. 1 and 2 illustrate an embodiment of the present invention, wherein a wheeled carriage is utilized to transport the cutting blade and its associated drive mechanisms to the desired sampling site. As illustrated hemispherical cutter 25 is located towards the forward end of the carriage. The opposite end of the carriage is defined by backend bulkhead 22, upon which is mounted bracket 67 for attachment of positioning handle 98 which is utilized to position the carriage by rolling on wheels 35 and 36. The front end of the carriage is supported by spring-biased front skid 75 (illustrated more completely in FIG. 11) which is biased by spring 78 to extend beyond the cutter 25 to protect the blade 48 from contacting the surface when the carriage is not secured in position. Front skid 75 is protected against overextension by spring retainer 77, mounted to backplate 79.

Figure 6:
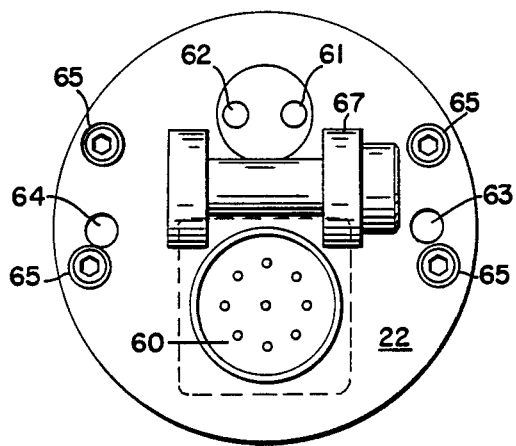
FIG. 6 is a back end view of a preferred embodiment of the present invention.
Figure 7:
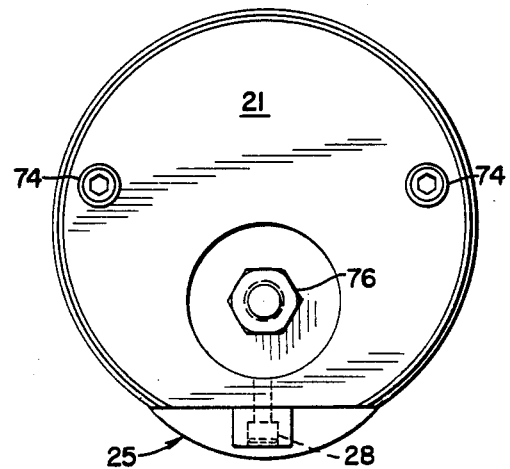
FIG. 7 is a front end view of a preferred embodiment of the present invention.
Figure 8:
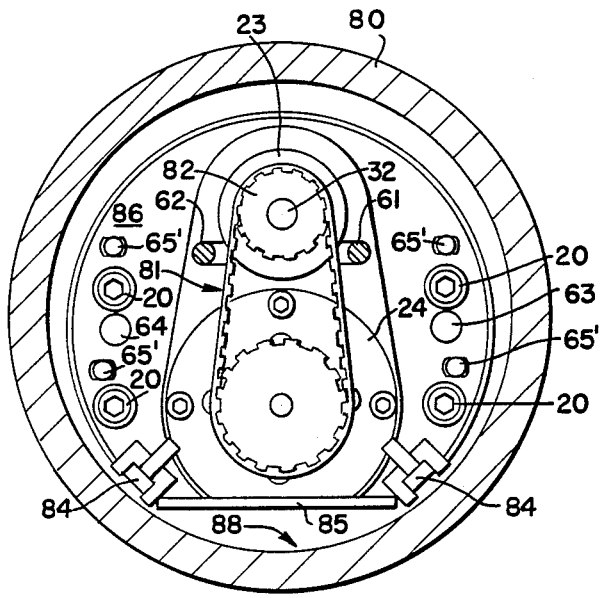
FIG. 8 is a cross sectional view taken along line 8—8 of FIGS. 1 and 2.

The backend bulkhead 22, as illustrated in FIG. 6, is bolted to the stepper motor housing 86 by bolts 65 which thread into holes 65' (as better illustrated in FIG. 8). Backend bulkhead 22 also has electrical connector 60 mounted thereon for receiving the electrical connector which carries the appropriate control signals for stepper motor 24 and drive motor 26. Bulkhead 22 has further openings for provision of coolant and vacuum lines 63 and 64 which extend the length of the carriage to provide coolant to the cutter 25 and the sampling area, and remove spent coolant from the region. Coolant access paths 63 and 64 extend throughout the length of the carriage, as can be seen in FIGS. 2 and 8-12.

Figure 10:
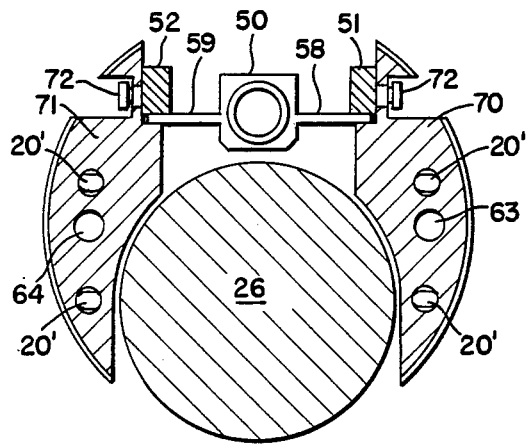
FIG. 10 is a cross sectional view taken along line 10—10 of FIGS. 1 and 2.

Stepper motor housing 87 is in turn bolted to the two drive motor housing members 70 and 71, illustrated in FIG. 10. Bolts 20 are utilized to secure the stepper motor housing 87 to the threaded holes 20' of the drive motor housing halves 70 and 71. As further illustrated in FIG. 8, stepper motor 24 is associated with toothed gear 83 and drive screw support bearing housing 23 is associated with drive screw toothed gear 82. Stepper belt 81 is utilized to link gears 82 and 83. The drive screw 32 is directly coupled to gear 82. As can be seen, Gear 83 is turned in controlled steps by controlled activation of stepper motor 24. Drive screw 32 is therefore rotated in precise discrete amounts through controlled actuation of stepper motor 24.

Figure 5:
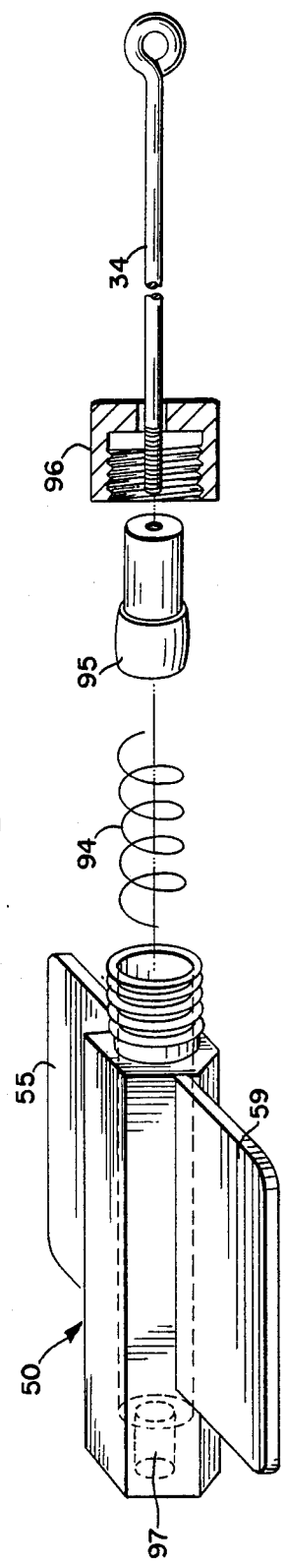
FIG. 5 is an assembly view of the rotational-to-linear motion translation assembly.
Figure 14:
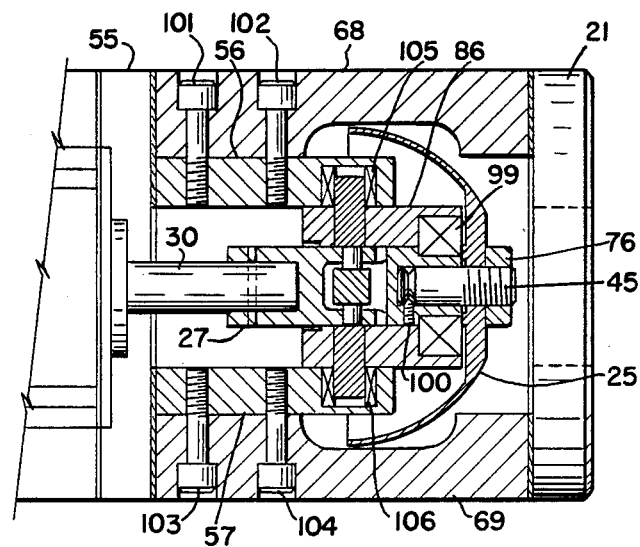
FIG. 14 is a top view of a horizontal cross-section of the cutting head taken at the cutter centerline.

Rotation of drive screw 32 is utilized to pivot cutter 25 into and out of engagement with the surface to be sampled. Drive screw 32 extends from gear 82 and into drive member 50. FIG. 5 illustrates the mechanism within drive member 50 for translation of the rotation of drive screw 32 into horizontal motion on push rod 34 to actuate the tilting of cutter 25 by pushing and pulling of arm 31 of the cutter trunnion 86 at pivot point 33. Push rod 34 will flex to accomodate the vertical motion of pivot point 33 that occurs due to its path of rotation. Trunnion 86 exerts force on the cutter shaft 45 through ring bearing 99 disposed between trunnion 86 and the cutter side of universal joint 27, in which shaft 45 is inserted and retained by set screw 100 (FIG. 14). The force of trunnion 86 therefore acts to tilt cutter 25 about the axis of trunnion bearings 105 and 106, which axis also passes through the center of action of universal joint 27, and the center of curvature of cutter 25.

The threaded end of drive screw 32 (illustrated in FIG. 1) is mated into the threaded hole 97 in one end of drive member 50. As drive screw 32 is rotated, drive member 50 will travel linearly along the longitudinal axis of drive screw 32. Drive member 50 is prevented from rotation by the engagement of wings 58 and 59 into the slots created between block 51 and drive motor housing member 70 and the block 52 and drive motor housing member 71 illustrated in FIG. 10. The wings 58 and 59 of drive member 50 slide along these slots to allow linear motion of drive member 50 while preventing its rotation.

Plunger 95 is threaded securely to the end of push rod 34, which extends through end cap 96. Plunger 95 is then inserted against biasing spring 94 inside the hollow portion of drive member 50. End cap 96 is then secured to the open end of drive member 50. This arrangement allows for compliance in the transmission of force from block 50 to push rod 34, to assure smooth advance of cutter 25 despite the incremental motion of block 50, as driven by stepper motor 24. Spring 94 allows some relative movement of plunger 95 within block 50. This compliance also acts to limit the force applied to pivot cutter 25. Blocks 51 and 52 are held in position by bolts 72.

Figure 9:
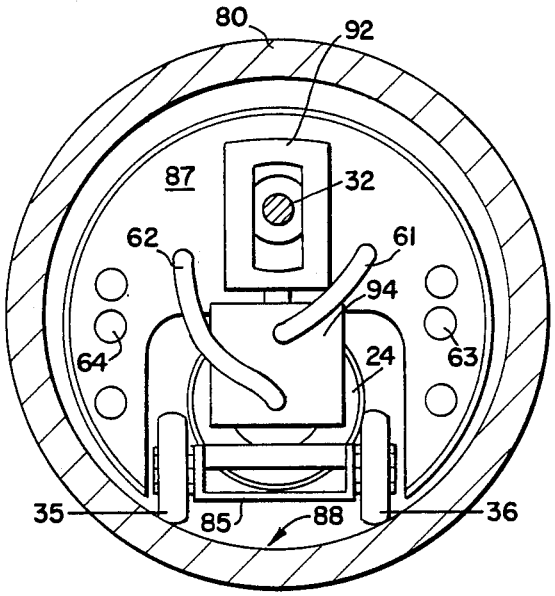
FIG. 9 is a cross sectional view taken along line 9—9 of FIGS. 1 and 2.

Wheels 35 and 36 as illustrated in FIG. 9, are mounted to an axle attached to spring plate 85. Plate 85 is attached at its opposite end to the stepper motor housing 86, thereby allowing the end to which the wheels 35 and 36 are attached to move upwardly and downwardly freely. Spring member 85 is biased so that wheels 35 and 36 will normally extend downwardly to extend beyond the outer circumference of the carriage, thereby contacting the surface upon which the carriage is riding.

Figure 11:
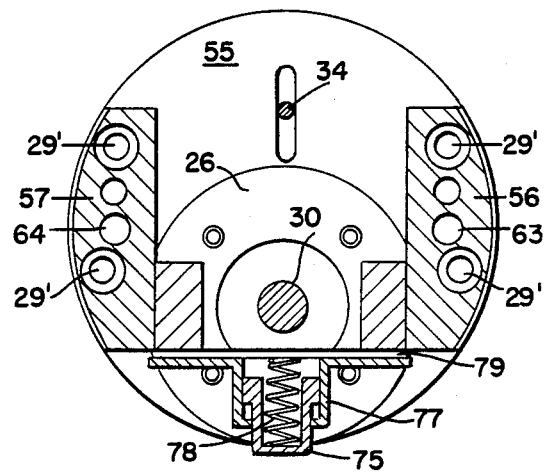
FIG. 11 is a cross sectional view taken along line 11—11 of FIGS. 1 and 2.
Figure 12:
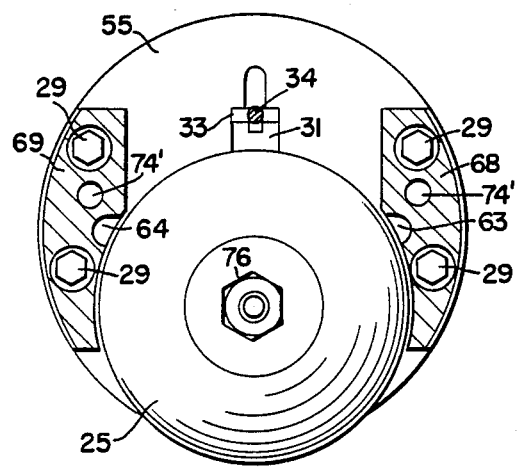
FIG. 12 is a cross sectional view taken along line 12—12 of FIGS. 1 and 2 of the present invention.

FIG. 11 illustrates the drive motor mounting bulkhead 55 to which the drive motor 26 is secured. Motor mount bulkhead 55 has an elongated slot through which pushrod 34 extends. Pushrod 34 then attaches to arm 31 at pivot 33, as illustrated in FIG. 12. Also in FIG. 12 the cutter 25 is shown secured to shaft 45 by nut 76. The cutter shaft 45 is linked to the drive motor shaft 30 through universal joint 27, thus allowing free pivoting of the cutter. Cutter support members 68 and 69 are bolted to the motor mount bulkhead 55 by bolts 29 illustrated in FIG. 12, which extend through holes 29' illustrated in FIG. 11, and are secured into threaded holes in the motor mount bulkhead 55. Similarly the front end bulkhead 21 is secured to the blade support members 68 and 69 by bolts 74, engaged in threaded holes 74'.

FIG. 14 illustrates that trunnion bearings 105 and 106 are housed by trunnion support members 56 and 57. Members 56 and 57 are attached to cutter support members 68 and 69 by capscrews 101 through 104.

The air cylinder 94 and pressure foot 92, utilized to lock the carriage in position for sampling, are illustrated in FIG. 9. Through proper control of air supply and return lines 61 and 62, air cylinder 94 is actuated to extend pressure foot 92 to engage the interior surface of a tube such as 80. Pressure foot 92 is slotted to permit passage of drive shaft 32.

Figure 13A:
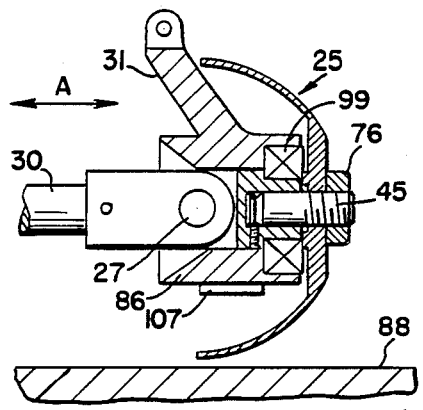
FIGS. 13A-E are simplified, partially schematized, views illustrating the present invention in use taking a sample from a surface.

The entire carriage is first positioned along the length of the tube by use of a rod 98 to push or pull the carriage in the directions indicated by arrow A (FIGS. 1, 2 and 13A) to the desired location. The carriage rolls along wheels 35 and 36, and slides along front skid 75, which prevents contact of the cutter 25 with the interior surface of the pipe 80. Once the carriage has been located in the desired position, pressure foot 92 is extended through actuation of air cylinder 94 and is forced into engagement with the upper interior surface of pipe 80. As pressure foot 92 continues to exert force, both front skid 75 and wheels 35 and 36 are forced to retract against their spring-biased mechanisms. The entire carriage will approach surface 88 until support pads 28, 83 and 84 contact the lower surface 88 of the interior of pipe 80. Support pads 28, 83 and 84 are adjusted prior to positioning of the mechanism, so that when the carriage is forced down against the pads, the carriage will rest a predetermined, desired distance off of the surface 88 to be sampled, which will determine the thickness of the sample to be removed.

Figure 13B:
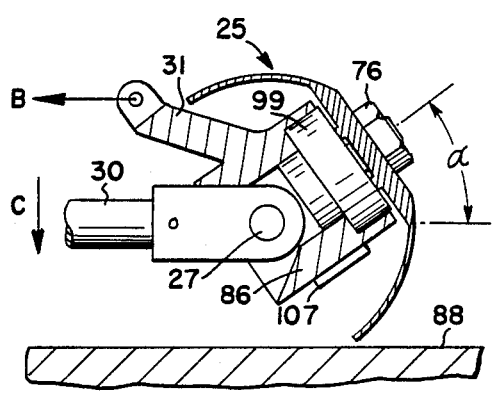
Figure 13C:
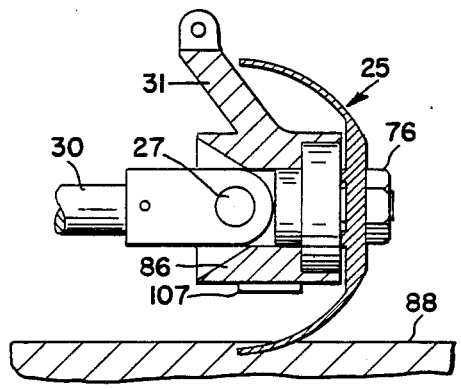
Figure 13D:
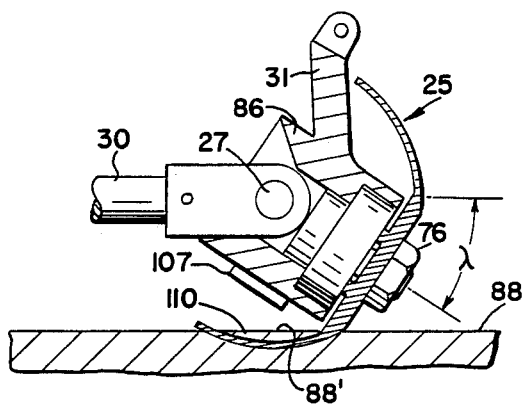
Figure 13E:
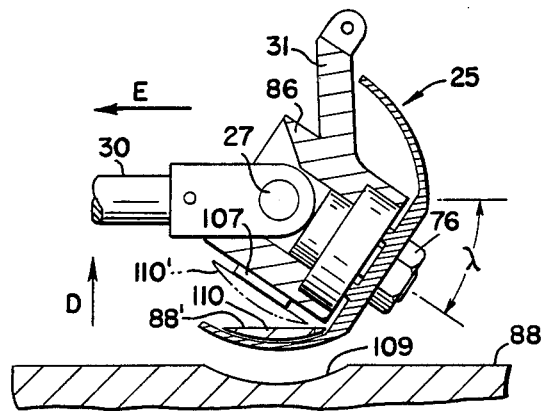

Once the carriage has been locked in position through force exerted by pressure foot 92 to cause the carriage to rest firmly on support pads 28, 83 and 84, the cutting process illustrated in FIGS. 13A–D may commence. Arrow A, (FIG. 13A) illustrates the horizontal positioning of cutter 25. Prior to being locked in position as described above, cutter 25 was retracted as illustrated in FIG. 13B in the direction of Arrow B. The entire carriage carrying cutter 25 is then forced in the direction of Arrow C against support pads 28, 83 and 84 by the clamping mechanism described above. After the positioning and clamping of the assembly, cutter 25 is then rotated in a direction opposite that of Arrow B from its retracted position. This is illustrated in FIG. 13C, i.e. a partial cut, and then sequentially in FIG. 13D, which is the final cut and separation of the sample to be collected and analyzed. This is accomplished, as aforesaid, through actuation of stepper motor 24 which rotates drive screw 32 to push pushrod 34, thereby tilting trunnion 86 through arm 31. Once the cut is complete, spinning of the cutter 25 is ceased by deactuation of drive motor 26. Cutter 25 remains in its fully-extended position, (FIG. 13D), in order to retain the extracted sample 110. For certain materials, a magnet 107 attached to the underside of trunnion 86 may be used to capture the sample, as indicated by position 110' in FIG. 13E. The pressure on pad 92 is relieved by deactuation of air cylinder 94. The carriage then raises up in the direction of Arrow D, (FIG. 13E), to ride once again on wheels 35 and 36 and front slide member 75. Cutter 25 is now clear of the interior surface of tube 80 and the carriage may be retreived in the direction of Arrow E, while cutter 25 is in its fully-extended position (FIG. 13E). Sample 110 is supported within the bowl of cutter 25 for retrieval (as illustrated in FIG. 13E).

Once extracted, the surface 88' of sample 110 can be analyzed. Also the sample 100 can be analyzed or tested for characteristics of the substrate material, thusly providing a means for analyzing both surface and material characteristics while leaving a minimally-disruptive dimple 109 in the original surface 88.

Blade 25 (as illustrated in FIG. 13B) is retractable through angle α wherein the axis of rotation of the blade is preferably about 30 to 32 degrees above horizontal. Similarly, as illustrated in FIGS. 13D and 13E, blade 25 is preferably designed to travel through angle λ below horizontal to complete the cut which severs sample 110. Angle λ is preferably about 30 to 32 degrees.

Figure 3:
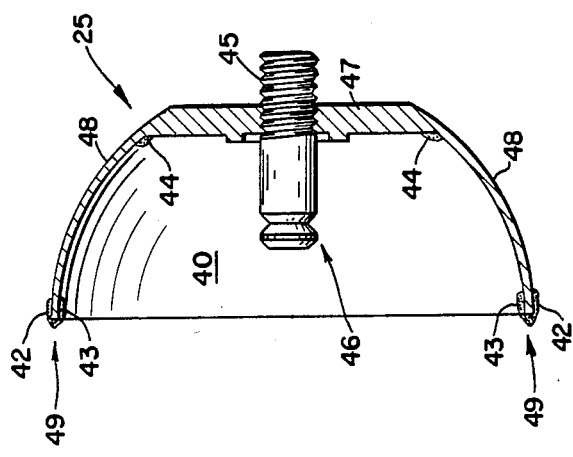
FIG. 3 is a cross-sectional side view of the hemispherical blade of a preferred embodiment of the present invention.

A particularly preferred embodiment of cutter 25 is illustrated in FIGS. 3 and 4 and is of a hemispherical shape, with a central, threaded hole to accomodate cutter shaft 45. Cutter shaft 45 has a notched end 46 for engagement by set screw 100 within universal joint 27. The cutter has a thick body portion 47 and a thin curved blade portion 48, which combine to form an essentially bowl-like structure. A thin coating of abrasive grit, which enables the blade to cut, is applied at the outer tip of the blade periphery, along the exterior surface at 42, along the interior at 43 and along the leading edge 49 of the blade. The entire length of the blade 48 is not provided with grit for cutting, so as to provide clearance for the noncutting portion of the blade and to minimize the opportunity for extraneous scratching of the surface of the sample or substrate. The very interior corner where the blade 48 meets the body 47 also contains a thin ring of cutting grit 44. This ring of grit 44 is provided to enable the first edge of a larger sample to be worn away, if necessary, thereby enabling the blade to obtain a deeper sample without jamming of the initial sample edge against the body 47 of the cutter 25.

Cutter 25 need not be precisely hemispherical, but can be comprised of a spherical section larger or smaller than a semi-(half) sphere. The cutter can be comprised of a spherical section greater than a hemisphere if a deeper, larger sample is desired. The cutter can also be comprised of a spherical section of less than hemispherical dimensions if a smaller, shallower sample is desired.

One significant beneficial result of the subject invention is the nature of the sample obtained for analysis. As can be seen in FIGS. 13C-E, once sample 110 has been cut and retrieved, it can be accurately analyzed, because the original surface 88' of the sample remains undisturbed on the sample's upper surface. Another beneficial result of the subject invention is the nature of the remaining substrate after the sample is cut from it. As can be seen, the removal of sample 110 leaves a rather small dimple 109 with a fine surface finish in the surface of the sampled substrate which causes minimal disruption and structural weakening of it. By minimizing the kerf left by the blade portion 48 of cutter 25, through utilization of a thin blade, the disruption of material 80 is further minimized. Because cutter 25 is hemispherical in design blade portion 48 can be constructed extremely thin while still providing a very rigid blade. In many embodiments, a kerf of between 0.020" and 0.025" may be achieved by using a blade of 0.010" thickness and fine layer of grit of about 0.005" in thickness on each side while the structural rigidity necessary to maintain an accurate sampling of steel is still maintained.

Once given the above disclosure many other features, modifications and improvements will become apparent to the skilled artisan. Such features, modifications and improvements are thus to be considered a part of this invention, the scope of which is to be determined by the following claims:

I claim:

1. A sampling device for cutting from a workpiece to be sampled a relatively small, preselected portion of the surface or surface and substrate of said workpiece and for retrieving said preselected portion for analysis apart from said workpiece without creating any substantial increase in stress in said workpiece whereby insufficient damage is caused to said workpiece to be detrimental to its continued use comprising:
    means for cutting and separating said preselected portion for analysis from said workpiece, said cutting means including a blade means of generally semi-spherical shape having an axis of rotation generally concentric with the center of said blade means,
    first drive means connected to said blade means for rotating said blade means about said axis,
    second drive means connected to said blade means for articulating said cutting means whereby said blade means is capable of cutting and separating said preselected portion for analysis from said workpiece by following a single arcuate path to create a relatively shallow, smooth depression in said workpiece, and
    means for retrieving said preselected portion for analysis when separated from said workpiece.
2. The device of claim 1, wherein:
    said semi-spherical blade is comprised of a thin, essentially hollow shell having an exposed circular edge.
3. The device of claim 2, further comprising:
    a first ring of cutting grit disposed on said circular edge, and extending onto the exterior surface of said shell immediately adjacent to said edge.
4. The device of claim 2 or claim 3, further comprising:
    a second ring of cutting grit disposed on the interior surface of said shell, adjacent said circular edge.
5. The device of claim 2 or claim 3, further comprising:
    a third ring of cutting grit disposed on the interior surface of said shell, a constant distance from said circular edge, and extending inwardly from said shell.
6. The device of claim 5, wherein:
    said third ring of cutting grit is provided to remove a portion of said sample at a sufficient distance from said circular edge to enable said cutter to travel a greater depth into said substrate.
7. The sampling device of claim 1 wherein said sampling device is capable of cutting and retrieving said preselected portion for analysis without any substantial alteration of said preselected portion.

8. The sampling device of claim 1 which further includes means for positioning said device at a selected position on the surface of said device from which said preselected portion is to be cut and for positioning said cutting means such that when said blade makes its cut by following the aforesaid arcuate path it initiates the cut by entering into the said surface at a first location thereof and finishes the cut by emerging from the same said surface but at a second location thereof.

9. The sampling device of claim 8 which further includes means for securing said cutting means at said selected position.

10. The sampling device of claim 9 wherein said securing means includes a suspension means for carrying and positioning said device, said suspension means normally biasing said device away from said surface and raising said cutting means out of engagement with said surface a sufficient distance to allow retrieval of said device after said cutting and separation of said portion from said surface, and further including means for overcoming said normal bias of said suspension which when actuated lowers said cutting means into cutting relationship with said surface against said normal bias of said suspension means.

11. The sampling device according to claim 10 wherein said means for overcoming the normal bias of said suspension means includes a fluid actuated cylinder means, and said device further includes adjustable means for adjusting the depth of the cut.

12. A sampling device for cutting from a workpiece to be sampled a relatively small, preselected portion of the surface or surface and substrate of said workpiece and for retrieving said preselected portion for analysis apart from said workpiece whereby insufficient damage is caused to said workpiece to be detrimental to its continued use comprising:
means for cutting and separating said preselected portion for analysis from said workpiece, said cutting means including a blade of generally semi-spherical shape having an axis of rotation generally concentric with the center of said blade,
first drive means connected to said blade for rotating said cutter about said axis,
second drive means connected to said blade for articulating said cutting means whereby said blade is capable of cutting and separating said preselected portion for analysis from said workpiece by following an arcuate path, and
means for retrieving said preselected portion for analysis when separated from said workpiece, and
wherein said retrieval means comprises said semi-spherical shaped blade.

13. The sampling device of claim 12 wherein said retrieval means further includes a magnet in proximal location to the internal surface of said semi-spherical shaped blade.

14. The sampling device according to claims 1, 7, 12, or 13 wherein said device is capable of cutting, separating and retrieving said preselected portion for analysis from an internal surface or surface and substrate of a generally hollow workpiece at a predetermined location within said workpiece and said retrieval means includes means for moving said device along said internal surface of said workpiece and withdrawing it from said hollow of said workpiece with said preselected portion for analysis confined within the confines of said device.

15. The sampling device of claim 14 wherein said arcuate path is a single arcuate path.

16. The sampling device of claim 15 wherein said workpiece is the component of a turbine generator system.

17. A sampling device capable of cutting, separating and retrieving a preselected portion of a workpiece to be analyzed, said portion being of a surface or surface and substrate of said workpiece and being located at a relatively confined and inaccessible location, the device comprising:
(a) a housing,
(b) a suspension system on which said housing rests which includes means for moving said housing along a surface to be sampled and means for biasing said moving means to a location external of said housing,
(c) means located within said housing, said means including:
(1) means for cutting and separating said preselected portion from said workpiece, said cutting means including a blade of generally semi-spherical shape having an axis of rotation generally concentric with the center of said blade,
(2) first drive means connected to said blade for rotating said cutter about said axis,
(3) second drive means connected to said blade for articulating said cutting means whereby said blade is capable of cutting and separating said preselected portion from said workpiece by following a generally arcuate path, and
(4) means for retrieving said preselected portion when separated from said workpiece.

18. A sampling device according to claim 17 wherein said suspension system includes a pair of wheels and a spring means associated with said wheels normally biasing said wheels in a direction so as to normally lift said cutting means above said surface a sufficient distance to allow retrieval of said device and said preselected portion after separation from said surface by said blade, and wherein said device further includes expandable and retractable fluid operated cylinder means located within said housing and capable of being expanded beyond said housing and being so located that upon expansion beyond said housing into engagement with a surface, continued expansion acts against said spring bias of said wheels thereby securing said device at that location on said surface and lowering said cutting means into cutting relationship with said preselected portion of said surface to be analyzed.

19. A sampling device according to claim 18 wherein said suspension system further includes an expandable and retractable slide member spaced from said wheels and a spring means normally biasing said slide member beyond said housing such that said housing is in part carried by said wheels and in part by said slide member, and such that upon said continued expansion of said fluid operated cylinder means against a surface, said slide member is caused to retract thereby further securing said device and allowing said lowering of said cutting means.

20. A sampling device according to claim 19 wherein said semi-spherical blade is comprised of a thin, essentially hollow shell having an exposed circular edge, said circular edge being provided with a cutting grit and a ring of cutting grit located at a preselected distance on an inner surface of said shell for grinding the forward edge of said portion if the length of said portion exceeds said preselected distance thereby to allow said cut to be completed.

21. A sampling device according to claim 20 further including means for remotely operating said first and second drive means, and means external of said housing for moving said device to its desired location.

22. A sampling device according to claim 17 or 26 wherein said housing is substantially cylindrical in shape and has an opening through which said blade means may be rotated to effect the cutting and separation of said portion to be analyzed.

23. A sampling device according to claim 22 wherein said device is capable of retrieving said portion for analysis from the internal surface of a pipe.

24. A sampling device according to claim 21 wherein said first drive means comprises in line a stepper motor, a drive screw means, a drive member for translating the rotation of the drive screw into horizontal motion of a pusher rod, and a pusher rod connected to said blade and horizontally operated by said drive member such that controlled actuation of said stepper motor causes said blade to be rotated in precise, predetermined amounts about its axis.

25. A sampling device according to claim 24 wherein said cutting means and second drive means include a drive motor, a shaft actuated by said drive motor and connected to a universal joint located internally of said blade means, said pusher rod being connected by connecting means to said blade internally of said blade such that actuation of said pusher rod causes said blade to rotate about the axis of said universal joint and actuation of said drive motor causes said shaft to rotate said blade and universal joint thereby effecting the cutting of a surface contacted by the blade, said connecting means being so arranged as to allow said blade and universal joint to be rotated for cutting without rotation of said connecting means or pusher rod connected thereto.

26. A sampling device according to claim 25 which further includes adjustable means associated with said housing for determining the depth of the cut to be made in the surface being analyzed.

27. A sampling device according to claim 26 capable of cutting, separating and retrieving said portion to be analyzed by initiating the cut at a first location on said surface and finishing said cut at a second location on the same said surface.

28. A sampling device according to claim 27 wherein said means for retrieving said preselected portion includes the internal surface of said semi-spherical blade.

29. A sampling device according to claim 28 wherein said retrieval means further includes a magnet located within the internal portion of said blade.

30. A sampling device according to claim 28 wherein said retrieval means consists essential of the internal surface of said semi-spherical blade.

* * * * *